US008809057B2

(12) United States Patent
Adler et al.

(10) Patent No.: US 8,809,057 B2
(45) Date of Patent: Aug. 19, 2014

(54) METHODS OF EVALUATING GENE EXPRESSION LEVELS

(75) Inventors: Aaron Daniel Adler, Sharon, MA (US); Jacob Stuart Michael Beal, Somerville, MA (US); Fusun Yaman-Sirin, Arlington, MA (US); Ron Weiss, Newton, MA (US); Noah Justin Davidsohn, Cambridge, MA (US)

(73) Assignee: Raytheon BBN Technologies Corp., Cambridge, MA (US)

( * ) Notice: Subject to any disclaimer, the term of this patent is extended or adjusted under 35 U.S.C. 154(b) by 140 days.

(21) Appl. No.: 13/343,504

(22) Filed: Jan. 4, 2012

(65) Prior Publication Data

US 2013/0171626 A1 Jul. 4, 2013

(51) Int. Cl.
*C12N 15/63* (2006.01)
*C12N 15/85* (2006.01)

(52) U.S. Cl.
USPC ..................... 435/455; 435/320.1; 435/325

(58) Field of Classification Search
None
See application file for complete search history.

(56) References Cited

U.S. PATENT DOCUMENTS

| 5,861,256 A | 1/1999 | Glass et al. |
| 5,880,473 A | 3/1999 | Ginestet |
| 2008/0034445 A1 | 2/2008 | Gambhir et al. |

FOREIGN PATENT DOCUMENTS

WO WO-2013103438 A1 7/2013

OTHER PUBLICATIONS

"International Application Serial No. PCT/US2012/063311, International Search Report mailed May 7, 2013", 7 pgs.
"International Application Serial No. PCT/US2012/063311, Written Opinion mailed May 7, 2013", 8 pgs.
Speicher, M. R, et al., "Karyotyping Human Chromosomes by Combinatorial Multi-Fluor Fish", Nature Genetics, 12, (Jan. 1, 1996), 368-375.
Tsurui, H., et al., "Seven-Color Fluorescence Imaging of Tissue Samples Based on Fourier Spectroscopy and Singular Value Decomposition", Journal of Histochemistry and Cytochemistry, 48(5), (2000), 653-662.
"International Application Serial No. PCT/US2012/063311, Invitation to Pay Additional Fees and Partial Search Report mailed Feb. 28, 2013", 8 pgs.
Fernandez-Lopez, R., et al., "Numbers on the edges: A simplified and scalable method for quantifying the Gene Regulation Function", *Bioessays*, 32(4), (Apr. 1, 2010), 346-355.
Kelly, J. R., et al., "Measuring the activity of BioBrick promoters using an in vivo reference standard", *Journal of Biological Engineering*, 3(1), (2009), 13 pgs.
Lee, T. S., et al., "BglBrick vectors and datasheets: A synthetic biology platform for gene expression", *Journal of Biological Engineering*, 5(1), (2011), 14 pgs.
"Biofab home page", [online]. [retrieved Nov. 2, 2012]. Retrieved from the Internet: <URL: http://biofab.org/>, (2012), 2 pgs.
"Professional Characterisation of Biological Parts", [online}. © 2012 Imperial College London, Centre for Synthetic Biology and Innovation. [retrieved Nov. 2, 2012]. Retrieved from the Internet: <URL: http://www3.imperial.ac.uk/syntheticbiology/parts>, (2012), 2 pgs.
Canton, B., et al., "Refinement and standardization of synthetic biological parts and devices", *Nature Biotechnology*, 26(7), (Jul. 2008), 787-793.
Ellis, T., et al., "Diversity-based, model-guided construction of synthetic gene networks with predicted functions", *Nature Biotechnology*, 27(5), (May 2009), 465-471.
Rosenfeld, N., et al., "Accurate prediction of gene feedback circuit behavior from component properties", *Molecular Systems Biology*, 3, (2007), 1-4.
Rosenfeld, N., et al., "Gene regulation of the single-cell level", *Science*, 307(5717), (2005), 1962-1965.
Weiss, R., "Cellular Computation and Communications using Engineered Genetic Regulatory Networks", *PhD Thesis, MIT*, (2001), 138 pgs.

*Primary Examiner* — Celine Qian
(74) *Attorney, Agent, or Firm* — Schwegman, Lundberg & Woessner, P.A.

(57) ABSTRACT

Described herein are methods of evaluating the expression levels of DNA parts encoding proteins in test circuits. In particular, the methods disclosed herein are useful to evaluate the expression of an output protein regulated by a regulatory protein-genetic element pair.

20 Claims, 13 Drawing Sheets a.

b.

a.

b.

Readings for the six good candidates amongst available filters

For each Source/Filter combination, the Read Channel is calibrated such that the "heat" measured in the Read Channel that matches the Filter is zero, shown below in the 11 framed boxes.

SEQUENCE LISTING

```
<160> NUMBER OF SEQ ID NOS: 1

<210> SEQ ID NO 1
<211> LENGTH: 22
<212> TYPE: PRT
<213> ORGANISM: Artificial Sequence
<220> FEATURE:
```

-continued

```
<223> OTHER INFORMATION: 2A Peptide

<400> SEQUENCE: 1

Gly Ser Gly Ala Thr Asn Phe Ser Leu Leu Lys Gln Ala Gly Asp Val
1               5                   10                  15

Glu Glu Asn Pro Gly Pro
            20
```

METHODS OF EVALUATING GENE EXPRESSION LEVELS

STATEMENT REGARDING FEDERALLY SPONSORED RESEARCH & DEVELOPMENT

This invention was made with government support under Contract No. HR0011-10-C-0168 awarded by the Defense Advanced Research Projects Agency. The government has certain rights in this invention.

BACKGROUND

A quantitative understanding of living cells will require methods to perturb and control the activities of their constituent proteins at fine spatial and temporal resolutions. By measuring responses to precise perturbations, predictive models of cellular networks can be tested and iteratively improved.

Genetic circuits provide a method to design and control perturbations, which contributes to the development of predictive models of cellular networks. Genetic circuits have been built that encode functions that are analogous to electronic circuits, and genetic programs have been built by combining multiple circuits. An understanding of the activity of genetic elements is important for the design and development of such circuits.

Disclosed herein are new methods of determining expression levels of test circuits, particularly expression levels of regulatory protein-genetic element pairs.

SUMMARY

In one embodiment, a method of evaluating the expression level produced by a test regulatory molecule-test genetic element pair, comprises providing a population of cells comprising an effector transcription unit comprising a constitutive effector genetic element and a coding sequence for an effector-regulated protein, wherein the constitutive effector genetic element controls expression of the effector-regulated protein, wherein the effector-regulated protein binds a genetic element responsive to the effector-regulated protein, and wherein the binding activity of the effector-regulated protein to the genetic element responsive to the effector-regulated protein is modulated by an input effector, a test regulatory molecule transcription unit comprising the genetic element responsive to the effector-regulated protein and a coding sequence for the test regulatory molecule, wherein the genetic element responsive to the effector-regulated protein controls expression of the test regulatory molecule, an input transcription unit comprising the genetic element responsive to the effector-regulated protein and a coding sequence for an input reporter protein, wherein the genetic element responsive to the effector-regulated protein controls expression of the input reporter protein, wherein the test regulatory molecule transcription unit and the input transcription unit are co-expressed from the same genetic element responsive to the effector-regulated protein, or are expressed separately from separate copies of the genetic element responsive to the effector-regulated protein, an output transcription unit comprising the test genetic element responsive to the test regulatory molecule and a coding sequence for an output reporter protein, wherein the test genetic element responsive to the test regulatory molecule controls expression of the output reporter protein, and a constitutive reporter protein transcription unit comprising a constitutive genetic element and a coding sequence for a constitutive reporter protein, wherein the constitutive genetic element controls expression of the constitutive reporter protein, incubating the cells at a plurality of amounts of the input effector for a time and under conditions sufficient to allow expression of the effector transcription unit, the test regulatory molecule transcription unit, the input reporter protein transcription unit, the output reporter protein transcription unit, and the constitutive reporter protein transcription unit, measuring the levels of the input reporter protein, the output reporter protein and the constitutive reporter protein in the individual cells of the population of cells, optionally performing signal compensation on the measured levels of the input reporter protein, the output reporter protein and the constitutive reporter protein to reduce signal overlap and produce a compensated level of input reporter protein, a compensated level of output reporter protein, and a compensated level of constitutive reporter protein, two-dimensionally binning the cells at each amount of the input effector into a plurality of bins by the uncompensated or compensated level of constitutive reporter protein to produce a finite number of binned cells, and calculating for each bin a bin average level of constitutive reporter protein, optionally normalizing, for the cells in each bin, the uncompensated or compensated level of output reporter protein and/or the uncompensated or compensated level of input reporter protein by the bin average level of constitutive reporter protein to produce a normalized level of input reporter protein and/or a normalized level of output reporter protein, and evaluating the expression level produced by the test regulatory molecule-test genetic element pair from the uncompensated, compensated, normalized or non-normalized level of input reporter protein and output reporter protein.

In another embodiment, a method of selecting three optical bandpass filter-fluorescent protein pairs for simultaneous fluorescent measurement comprises a) selecting a plurality of optical bandpass filters and a plurality of fluorescent proteins, b) measuring the emission for each of the plurality of fluorescent proteins with each of the plurality of optical bandpass filters and scaling the emission from cold to hot, wherein cold represents low emission and hot represents high emission for each optical bandpass filter-fluorescent protein combination, c) building a two-dimensional matrix for the scaled emission for each of the plurality of fluorescent proteins with each of the plurality of optical bandpass filters, d) selecting a first test fluorescent protein and identifying a first test optical bandpass filter for the first test protein that is as hot as possible for the test fluorescent protein in the two dimensional matrix while being cold for at least a second and a third test fluorescent protein to produce a first fluorescent protein-optical bandpass filter combination, e) repeating step d) for the second and the third test fluorescent proteins to produce second and third fluorescent protein-optical bandpass filter combinations, and f) selecting the first, second and third selected optical band-pass filter-fluorescent protein combinations for simultaneous measurement of three fluorescent proteins.

The above-described and other features will be appreciated and understood by those skilled in the art from the following detailed description, drawings, and appended claims.

DETAILED DESCRIPTION

In one aspect, provided herein are methods of evaluating the expression levels of DNA parts regulating protein expression in test circuits. In particular, the methods disclosed herein are useful to evaluate the expression of an output protein regulated by a regulatory molecule-genetic element pair. DNA part characterization is a fundamental aspect of synthetic biology wherein the goal is to be able to employ standardized parts to produce predicable device design. However, there have been substantial difficulties with obtaining accurate measurements of relevant chemical properties within individual cells. In addition, there is a challenge in predicting the behavior of a DNA part when it is used in a novel circuit design. By employing methods suitable for high-throughput characterization as described herein, DNA part characterization can be performed faster and more accurately than in previous methods.

Figure 1:
FIG. 1 shows the prior art characterization process for DNA circuits using integration into the chromosome (a) and the normalized method of the present disclosure wherein transfection of multiple circuits is performed in a first step allowing for fast collection of data (b).
Figure 1:
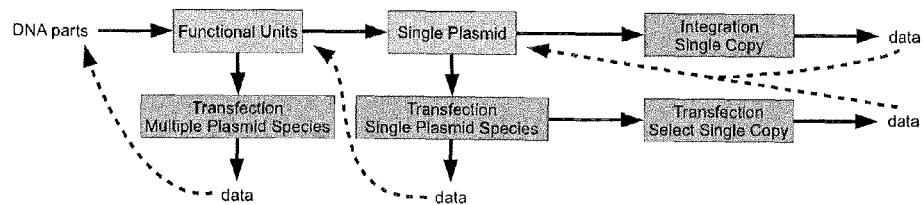

One challenge to overcome in the development of high-throughput methods for DNA part analysis is the lack of control of the copy number of the plasmids containing the DNA parts to be studied. In mammalian transfection, multiples copies of a plasmid enter a cell, often varying over 2-3 orders of magnitude. Thus, there are significant challenges in controlling for the copy number of the plasmids in cells. As shown in FIG. 1a, previously, in order to control for copy number of the test circuit, the test circuit was integrated into the chromosome of the cell to ensure one or two copies of the test circuit would be produced in each cell. Input/output transfer curves could be obtained by growing many colonies of cells under different conditions, e.g., different levels of inducer, and then measuring reporter levels, e.g., fluorescence, in single cells. This method is laborious and error-prone. As shown in FIG. 1b, in the method described herein, transfection of multiple circuits can be performed in a first step, allowing for a fast collection of data under a variety of conditions. Then in a second step, promising circuits can be integrated and studied, however, the initial screen should improve the chances of careful study of a successful circuit. Another advantage of the methods described herein is that the test circuit can be in the same plasmid, or split into separate plasmids for study.

Figure 2:
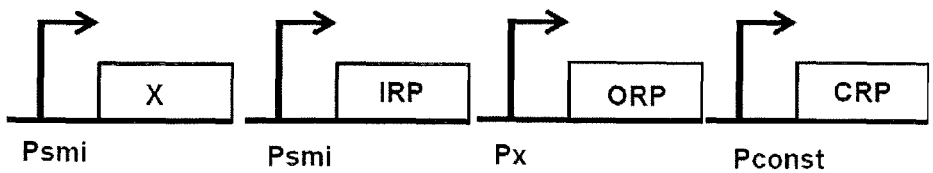
FIG. 2 shows a schematic of a circuit with a copy count indicator.

While the number of plasmids that enter a cell cannot be controlled, the number of plasmids in the cell can be measured by modifying the circuit to contain a copy count indicator, which is a constitutive reporter protein (CRP) under control of a constitutive genetic element such as a promoter, Pconst, as illustrated in one embodiment in FIG. 2. The reporter protein is a fluorescent protein, for example, and fluorescence can be measured using a FACS analysis. In FIG. 2, X is a test regulatory protein which binds to the test genetic element Px, wherein production of test protein X is regulated by a genetic element that is responsive to a small molecule effector, Psmi. The production of an input reporter protein (IRP) is also regulated by Psmi, so that the concentrations of X and IRP are closely related. The production of the output reporter protein (ORP) is controlled by the binding of X to Px, a test genetic element. Thus, the system contains three reporters, an input reporter protein, an output reporter protein, and a constitutive reporter protein.

As used herein, a "reporter" gene or protein is any gene or protein that is easily detectable and measurable. Exemplary reporter proteins include, e.g., fluorescent proteins, chemiluminescent proteins, proteins that can be detected by immunostaining, and radioactively-labeled proteins.

Exemplary fluorescent proteins include, e.g., enhanced blue fluorescent protein (EBFP), enhanced blue fluorescent protein-2 (EBFP2), mKATE, iRFP (infrared fluorescent protein), enhanced yellow fluorescent protein (EYFP), yellow fluorescent protein (YFP), Katushka, Ds-Red express, TurboRFP, TagRFP, green fluorescent protein (GFP), blue fluorescent protein (BFP), cyan fluorescent protein (CFP), enhanced green fluorescent protein (EGFP), AcGFP, TurboGFP, Emerald, Azami Green, ZsGreen, Sapphire, T-Sapphire, enhanced cyan fluorescent protein (ECFP), mCFP, Cerulean, CyPet, AmCyan1, Midori-Ishi Cyan, mTFP1 (Teal), Topaz, Venus, mCitrine, YPet, PhiYFP, ZsYellow1, mBanana, Kusabira Orange, mOrange, dTomato, dTomato-Tandem, DsRed, DsRed2, DsRed-Express (T1), DsRed-Monomer, mTangerine, mStrawberry, AsRed2, mRFP1, JRed, mCherry, HcRed1, mRaspberry, HcRed1, HcRed-Tandem, mPlum, and AQ143.

Fluorescent proteins can be assayed, e.g., by FACS or fluorescence microscopy.

In one embodiment, the constitutive reporter is mKATE, the input reporter is enhanced blue fluorescent protein-2 (EBFP2) and the output reporter is enhanced yellow fluorescent protein (EYFP).

Other exemplary reporter proteins include beta-galactosidase (encoded by the lacZ gene), a polypeptide comprising a detectable protein tag, such as a FLAG tag or HISx6 tag, a c-myc tag or a HaloTag® (Promega Corporation).

Reporter gene expression can be assayed by immunohistochemistry, e.g., by detecting expressed proteins with antibodies labeled with different detectable probes (e.g., Alexa Fluor®, Oregon Green® or Pacific Blue®; horseradish peroxidase (HRP) and alkaline phosphatase (AP)). In one embodiment, beta-galactosidase is assayed using X-Gal substrate.

In one embodiment, a test reporter protein and a control reporter protein can be labeled with different radioisotopes, e.g., $^{32}P$, $^{125}I$ or $^{35}S$, such as by culturing cells in the presence of the isotopes. The differential labeling of the different isotopes on the control and test reporter proteins can be assayed, e.g., by mass spectrometry.

In one embodiment, a method of evaluating the expression level produced by a test regulatory molecule-test genetic element pair comprises
providing a population of cells comprising
an effector transcription unit comprising a constitutive effector genetic element and a coding sequence for an effector-regulated protein, wherein the constitutive effector genetic element controls expression of the effector-regulated protein, wherein the effector-regulated protein binds a genetic element responsive to the effector-regulated protein, and wherein the binding activity of the effector-regulated protein to the genetic element responsive to the effector-regulated protein is modulated by an input effector,
a test regulatory molecule transcription unit comprising the genetic element responsive to the effector-regulated protein and a sequence for the test regulatory molecule, wherein the genetic element responsive to the effector-regulated protein controls expression of the test regulatory molecule,
an input transcription unit comprising the genetic element responsive to the effector-regulated protein and a coding sequence for an input reporter protein, wherein the genetic element responsive to the effector-regulated protein controls expression of the input reporter protein,
wherein the test regulatory molecule transcription unit and the input transcription unit are co-expressed from the same genetic element responsive to the effector-regulated protein, or are expressed separately from separate copies of the genetic element responsive to the effector-regulated protein
an output transcription unit comprising the test genetic element responsive to the test regulatory molecule and a coding sequence for an output reporter protein, wherein the test genetic element responsive to the test regulatory molecule controls expression of the output reporter protein, and
a constitutive reporter protein transcription unit comprising a constitutive genetic element and a coding sequence for a constitutive reporter protein, wherein the constitutive genetic element controls expression of the constitutive reporter protein,
incubating the cells at a plurality of amounts of the input effector for a time and under conditions sufficient to allow expression of the effector transcription unit, the test regulatory molecule transcription unit, the input reporter protein transcription unit, the output reporter protein transcription unit, and the constitutive reporter protein transcription unit,
measuring the levels of the input reporter protein, the output reporter protein and the constitutive reporter protein in the individual cells of the population of cells,
optionally performing signal compensation on the measured levels of the input reporter protein, the output reporter protein and the constitutive reporter protein to reduce signal overlap and produce a compensated level of input reporter protein, a compensated level of output reporter protein, and a compensated level of constitutive reporter protein,
two-dimensionally binning the cells at each amount of the input effector into a plurality of bins by the uncompensated or compensated level of constitutive reporter protein to produce a finite number of binned cells, and calculating for each bin a bin average level of constitutive reporter protein,
optionally normalizing, for the cells in each bin, the uncompensated or compensated level of output reporter protein and/or the uncompensated or compensated level of input reporter protein by the bin average level of constitutive reporter protein to produce a normalized level of input reporter protein and/or a normalized level of output reporter protein, and
evaluating the expression level produced by the test regulatory molecule-test genetic element pair from the uncompensated, compensated, normalized or non-normalized level of input reporter protein and output reporter protein.

In one embodiment, evaluating the expression level produced by the test regulatory molecule-test genetic element pair is done by producing an input effector transfer curve of the non-normalized or normalized level of input reporter protein versus the amount of input effector, and/or producing a regulatory molecule transfer curve of the non-normalized or normalized level of output reporter protein versus the non-normalized or normalized level of input reporter protein and evaluating the expression level produced by the test regulatory molecule-test genetic element pair from the input effector transfer curve and/or the regulatory molecule transfer curve.

One embodiment of a test regulatory molecule transcription unit, input transcription unit, output transcription unit and constitutive transcription unit is illustrated in FIG. 2. An advantage of the methods described herein is that all transcription units can be provided separately, e.g., on separate plasmids, and transfected in a multiplex transfection manner. The binning and normalization procedures described herein allow for extraction of useful data from a complex system.

The effector transcription unit, test regulatory molecule transcription unit, and/or input transcription unit can further comprise coding sequences for additional regulatory proteins and or coding sequences for other proteins to be tested. For example, regulatory proteins can bind cofactors such as enhancers which attenuate their activity. The cofactors can be encoded on one or more of the transcription units.

Suitable cells for use in assaying test genetic elements include eukaryotic cells (e.g., yeast, fungi, insect, plant, mammalian, or nucleated cells from other multicellular organisms) and prokaryotic cells (e.g., *E. coli* (*Escherichia coli*), *Bacillus subtilis*). Exemplary mammalian cells include Hek293, CHO (Chinese Hamster Ovary Cells), 3T3, HeLa, COS-7, Balb/c, and the like.

Suitable plasmids for evaluating a transcription unit can include a selection gene, also called a selectable marker. Typical selection genes encode proteins that (a) confer resistance to antibiotics or other toxins, e.g., ampicillin, neomycin, streptomycin, methotrexate, or tetracycline; (b) complement auxotrophic deficiencies; or (c) supply critical nutrients not available from complex media, e.g., the gene encoding D-alanine racemase for *Bacilli*.

Optionally, suitable selectable markers for mammalian cells are those that enable the identification of cells competent to take up the plasmid(s) comprising the test and control promoters, such as Dihydrofolate reductase (DHFR), neo, glutamic-pyruvate transaminase (gpt), hygromycin (hygro), thymidine kinase (tk), hypoxanthine-guanine phosphoribosyltransferase (hgprt), or adenine phosphoribosyltransferase (aprt). An appropriate host cell when wild-type DHFR is employed is the CHO cell line deficient in DHFR activity. A suitable selection gene for use in yeast is the trp1 gene present in the yeast plasmid YRp7. The trp1 gene provides a selection marker for a mutant strain of yeast lacking the ability to grow in tryptophan, for example, ATCC No. 44076 or PEP4-1.

There are a variety of techniques available for introducing nucleic acids into viable cells, e.g., for introducing a plasmid comprising a transcription unit, or multiple plasmids/transcription units, into cells. Techniques suitable for the transfer of nucleic acid into mammalian cells in vitro include the use of liposomes, electroporation, microinjection, cell fusion, DEAE-dextran, calcium phosphate precipitation method, and the like. A variety of known methods, including electroporation or calcium chloride methods can be used to transfer nucleic acids into prokaryotic cells, e.g., *E. coli*.

In one embodiment, a virus is used to deliver nucleic acids into a cell.

As used herein, an input effector is a signal that controls expression of the effector-regulated protein. The amount, e.g., the concentration, of the input effector regulates the expression of the effector-regulated protein. Exemplary effectors include physical signals, e.g., light, and small molecules.

In one embodiment, the input effector is a small molecule effector. The cells are incubated with a plurality of concentrations of the small molecule effector for a time and under conditions sufficient to allow expression of the effector transcription unit, the test regulatory protein transcription unit, the input reporter protein transcription unit, the output reporter protein transcription unit and the constitutive reporter protein transcription unit. Exemplary conditions include the conditions described in the examples herein. In a specific embodiment the concentration of small molecule effector often varies over 2-3 orders of magnitude.

Figure 3:
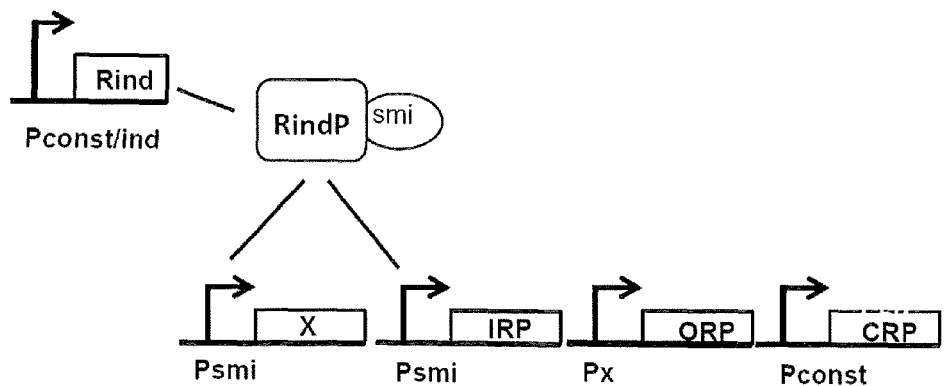
FIG. 3 shows a schematic of a circuit including the effector transcription unit.

FIG. 3 illustrates an embodiment of an effector transcription unit, a test regulatory protein transcription unit, an input reporter protein transcription unit, an output reporter protein transcription unit, and a constitutive reporter transcription unit, and shows the regulation of the test regulatory protein and input reporter transcription units by the small molecule effector.

Another embodiment might use the light sensor developed by Levskaya et. al (Levskaya, A., Chevalier, A. A., Tabor, J. J., Simpson, Z. B., Lavery, L. A., Levy, M., Davidson, E. A., Scouras, A., Ellington, A. D., Marcotte, E. M., & Voigt, C. A. "Synthetic biology: Engineering *Escherichia coli* to see light." Nature, 438: 441-442.) and light as the effector. One implementation might use parts BBa_I15008, BBa_I15009, BBa_I15010 from the MIT Registry of Standard Biological Parts in *E. coli*.

Exemplary constitutive genetic elements for both the effector transcription unit and the constitutive reporter transcription unit include the phef1A promoter, the pCAG promoter, the PGK (phosphoglycerate kinase 1) promoter, or a CMV promoter.

The effector transcription unit includes a coding sequence for an effector-regulated protein which binds a genetic element responsive to the effector-regulated protein. Exemplary effector transcription units include the tetracycline inducible or repressible systems which are regulated by a tetractycline antibiotic such as doxycycline. In the TetOff system, the tetracycline transactivator (tTA) protein binds to the tet operator, thus activating nearby genes. Binding to a tetracycline antibiotic prevents rTA from binding DNA, thus turning off gene activation. In the tetOn system, the rtTA protein is capable of binding the operator only when bound by a tetracycline antibiotic. Thus, nearby genes are activated only in the presence of a tetracycline antibiotic. Other effector transcription units known in the art include the a promoter operably linked to a lac operator (LacO), a LoxP-stop-LoxP system promoter, or a GeneSwitch™ or T-REx™ system promoter (Invitrogen), or equivalents thereof with identical or substantially similar mechanisms. In another embodiment the effector transcription unit includes the RheoSwitch system in which the Rheoreceptor and Rheoactivator proteins are activated by the presence of RSL1 ligand. In the presence of the RSL1 ligand, the receptor and activator stably dimerize and bind to the response element and turn on transcription.

Figure 9:
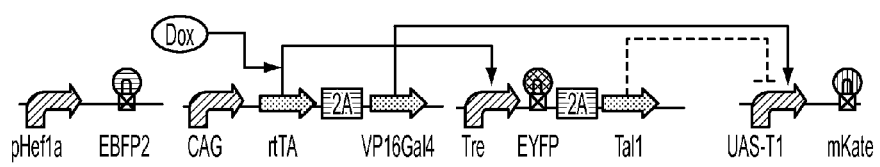
FIG. 9 shows the test circuit for Example 2.

In another embodiment, the inducible/repressible system includes the Gal4 system as illustrated in FIG. 9.

As used herein, a test regulatory molecule is a protein, nucleic acid or combination thereof (e.g., LacI+miRFF4) that binds to a test genetic element and regulates protein expression at the transcriptional or the post-transcriptional level. In one embodiment, the test regulatory molecule is a regulatory protein that regulates transcription by binding to a DNA sequence such as a promoter or an upstream activating sequence. Exemplary test regulatory proteins include LacI and Tal1. If the test regulatory molecule is a protein, the test regulatory molecule transcription unit includes a coding sequence for the protein.

In another embodiment, the test regulatory molecule is an RNA molecule such as an miRNA or an siRNA molecule that regulates transcription at the post-transcriptional level. If the test regulatory molecule is a nucleic acid, the test regulatory molecule transcription unit includes a sequence for the nucleic acid. A microRNA (miRNA) is a short RNA molecule, about 22 nucleotides, that binds to a complementary sequence on a messenger RNA, the test genetic element, and post-transcriptionally regulates translation, through, for example, translational repression, target degradation or gene silencing. A small interfering RNA (siRNA) is a short-interfering or silencing RNA that base pair to a complementary sequence in a target mRNA and induce cleavage of the mRNA, thus preventing translation. Thus in the case of miRNA and siRNA, the test genetic element is a sequence that is complementary to the miRNA or the siRNA.

The test regulatory molecule transcription unit and the input transcription unit are either co-expressed from the same genetic element responsive to the effector-regulated protein, or are expressed separately from separate copies of the genetic element responsive to the effector-regulated protein. That is, the test regulatory molecule transcription unit and the input transcription unit can be on the same plasmid or on separate plasmids. In order to provide bicistronic or multicistronic expression vectors, an internal ribosome entry site (IRES) can be used. However, differences have been noted in the expression levels between genes before and after the IRES. An alternative is to use a self-cleaving 2A peptide, an 18-22 amino acid peptide that, when translated, leads to skipping of a glycyl-prolyl bond at the C-terminus and cleavage between the 2A peptide and its immediate downstream peptide. An exemplary 2A peptide is P2A, GSGATNFS-LLKQAGDVEENPGP (SEQ ID NO: 1).

In certain embodiments, the cells contain additional transcription units that allow for varying degrees of control/expression of the input and output reporters.

Figure 14:
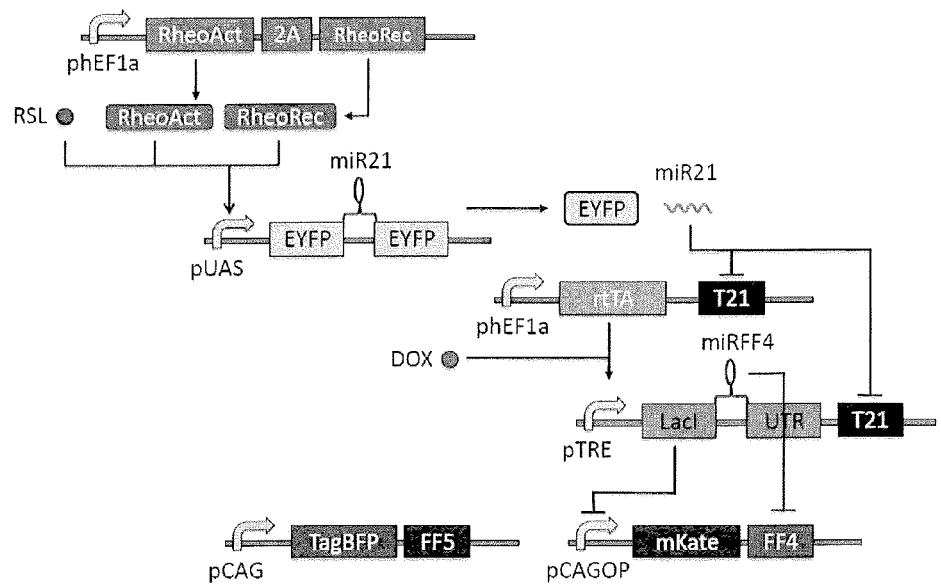
FIG. 14 shows an embodiment of an miRNA circuit, the miR21 high circuit.

In one embodiment, the output transcription unit comprises a plurality of linked transcription units. Each transcription unit in the plurality of linked transcription units contains a promoter and one or more sequences that links the test regulatory molecule-test genetic element pair to the production of the output reporter protein. That is, the output reporter protein and the test genetic element need not be on the same transcription unit so long as they are linked. FIG. 14 shows an example of a linked output reporter transcription unit.

Once expression of the transcription units has occurred, the levels of the input reporter protein, the output reporter protein and the constitutive reporter protein are measured. Preferably, measurement is at the single cell level, using a technique such as flow cytometry. In flow cytometry, a beam of light such as laser light is directed into a hydrodynamically-focused stream of liquid containing particles to be measured, e.g., cells. A plurality of detectors are used to measure reporters in the particles as they pass through. Fluorescent labels, chemiluminescent labels, quantum dots and isotopic labels can be measured using flow cytometry.

In one embodiment the reporter is a fluorescent reporter. In this embodiment, measurement is performed by FACS (fluorescence activated cell sorter) analysis. FACS is a type of flow cytometry in which reporter signals from single cells can be measured. By using multiple wavelength filters, multiple reporters can be measured from the same sample.

Once the levels of the three reporter proteins are measured in the individual cells, signal compensation is optionally performed on the measured levels of the input reporter protein, the output reporter protein and the constitutive reporter protein to reduce signal overlap and produce a compensated level of input reporter protein, a compensated level of output reporter protein, and a compensated level of constitutive reporter protein. In the case of fluorescence measurements, color compensation is a method in which the fluorescence spillover originating from one fluorophore other than the one being detected is subtracted from the one being detected, usually as a subtraction. Fluorescence compensation minimizes fluorescence spectral overlap and measure the true emission of each fluorochrome. While the constitutive, input and output reporters are selected to have minimal overlap in their emission spectra, some spillover or overlap is typically present. Color compensation can be particularly important when multiple reporters are measured simultaneously. Also, color compensation can be important when there is a large difference in expression levels. For example, a 1% bleedover is significant when there is a 100-fold difference in expression level.

Color compensation is typically done by examining the emission spectra for the constitutive, input and output reporters and determining the amount of spectral overlap. Compensation can be linear, wherein a percentage is subtracted from each measured value, or non-linear, such as a performing a piecewise linear fit of the data. The term non-linear compensation includes a piecewise linear fit, in which the expression of a color is measured on two FACS laser/filter combinations, one of which is the primary channel and one of which is the channel to be compensated. It may be useful to use an input effector like a small molecule inducer in order to get sufficient range of expression of the fluorescent protein. The data is segmented into bins on the primary channel value, then mean and standard deviation of points within that bin are measured on the channel to be compensated. This information forms the non-linear model. In order to perform compensation, a set of measurements Is taken and solved for a set of primary channel expression values that would superpose to produce the measured set of raw measurements (e.g., by iteration until convergence).

Color compensation also includes autofluorescence compensation, that is, compensating for the autofluorescence of the cells themselves.

Figure 4:
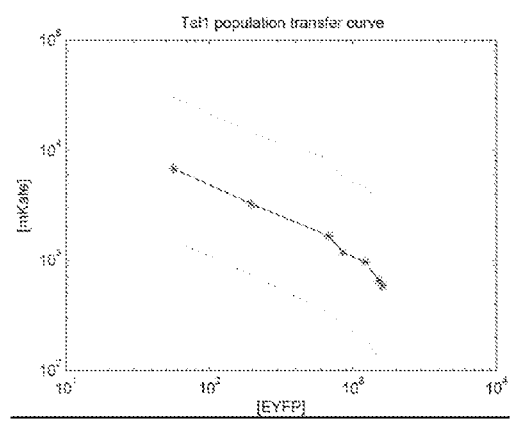
FIG. 4 shows characterization data from a Tal1 repressor from a multiple plasmid species circuit. Under prior methods (a), the measured transfer curve is essentially flat with no statistically significant repression, such that no meaningful data can be recovered. With the normalized characterization using binning as described herein (b), 100-fold repression with a 3-5× deviation in individual cell behavior is observed.
Figure 4:
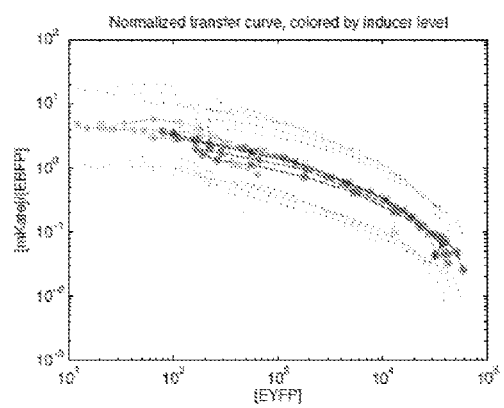

While the test circuits described herein including an input reporter and output reporter and a constitutive reporter allow one to correct for plasmid copy count, plasmid copy count correction based on a cell-by cell basis can produce a poor estimate of induction level. The inventors of the present application have unexpectedly found that by binning the cells by induction level of the input and output reporter and constitutive reporter level, the cells can be grouped into collections that have substantially similar input and output expression levels. Thus working within the means and variances of these groups and normalizing again, the mean constitutive fluorescence provides a characterization curve that allows for the extraction of meaningful data. FIG. 4 (a) shows data taken on a cell by cell basis, grouped by the inducer level and then averaged, which shows no statistically significant repression, and data normalized by the methods described herein (b) which shows 100-fold repression over a 3-5× standard deviation.

Thus, the method includes two-dimensionally binning the cells at each amount of the input effector into a plurality of bins by the compensated level of constitutive reporter protein to produce a finite number of binned cells, and calculating for each bin a bin average level of constitutive reporter protein. The bins can be equally spaced, but this is not necessary. In addition, the term bin average, as used herein, means the average over all of the cells in the bin, the bin center, or the level for a single cell in the bin. It has been determined that the average of cells in the bin, the bin center and a single cell in the bin generally provides similar results. Exemplary numbers of bins include 8, 9, 10, 11, 12, 13, 14, 15, 16, 17, 18, 19 and 20 bins, for example. In one embodiment, the bins are relatively narrow, e.g., 0.25 orders of magnitude, however, variable sizes can allow one to optimize the bin counts. By binning the cells by induction level and constitutive fluorescence level, the bins or collections of cells should have substantially the same input and output fluorescence levels. Analyzing the bins allows for the generation of characterization curves wherein statistically significant levels of repression or activation can be analyzed.

Once the cells are binned, the input and/or output protein levels are optionally normalized by the average level of the constitutive reporter for the bin. As explained above, the bin average is the average over all of the cells in the bin, the bin center, or the level for a single cell in the bin. Thus, the method includes optionally normalizing for the cells in each bin the uncompensated or compensated level of output reporter protein and/or the uncompensated or compensated level of input reporter protein by the bin average level of constitutive reporter protein to produce a normalized level of input reporter protein and/or a normalized level of output reporter protein. Normalization allows one to account for the multiple plasmid copies in the system.

After optional normalization, transfer curves are produced. In general, a transfer curve plots the signal output versus the signal input of a system and provides a graphical representation of the performance of a system. The method thus further comprises producing an input effector transfer curve of the normalized level of input reporter protein versus the amount of small molecule effector, and/or producing a normalized regulatory protein transfer curve of the normalized level of output reporter protein versus the compensated level of input reporter protein. These transfer curves allow one to evaluate the expression levels of the test regulatory molecule-test genetic element pair, that is, the strength of the activation or repression at various input levels.

Plotting the transfer curves visualizes the data so that the humans can evaluate the quality of the data. The data, which can be used without plotting, can be applied to a wide variety of modeling, simulation, prediction, and design tasks. Examples of such tasks include: automatically inferring transition (inflection) points, selection of genetic parts with compatible expression level, in order to construct a composite system for some designed purpose; selection of alternate realizations of a system that should be equivalent, in order to accelerate the realization of a desired system, simulation of the behavior of biological systems; debugging of a system that is not operating as expected, and study of biological phenomena, such as metabolic loading a response to changes in environmental conditions.

In one embodiment, disclosed herein in a method of identifying three reporters, such as three fluorescent proteins, for use in methods such as those described herein. Fluorescent proteins, for example, respond to and emit color across a significant fraction of the spectrum. This means that a few percent of the measured level of one fluorescent protein will be added to the level of another fluorescent protein. Prior correction models have been linear and provided no estimate of the accuracy of correction. The heat map color selection provided herein is derived from empirical data and provides a piecewise non-linear model that better matches actual interference and allows variance estimates that can be used to determine whether interference is correctable.

A heat map is a graphical representation of data wherein values of a variable in a two-dimensional table are represented as colors. There are many commercially available software packages that facilitate the building of data into a heat map.

In a FACS analysis, the emission of fluorescent markers such as fluorescent proteins in individual particles, e.g., cells, is measured at different wavelengths. Fluorescence emission at a particular wavelength is measured using an optical bandpass filter. An optical bandpass filter is an optical device that allows frequencies within a certain range to pass through it and rejects (attenuates) frequencies outside that range. For example, a 525 nm band pass filter will only allow "green" light to pass through to the detector. However, a problem with measuring multiple fluorophores or fluorescent proteins in the same experiment is bleed-over (also called bleed-through or crosstalk) that occurs due to spectral overlap. The mid-range bleed-over for a particular fluorescent marker-optical bandpass filter combination is defined as the average percentage bleed for a range which is neither close to the saturation of the instrument nor the auto-fluorescence level as measured by the instrument which can be determined in several ways. For this instance, the range is $10^{3.8}$ (approximately 6310) and $10^{4.5}$ (approximately 31623).

A method of selecting three optical bandpass filter-fluorescent protein pairs for simultaneous fluorescent measurement comprises
  a) selecting a plurality of optical bandpass filters and a plurality of fluorescent proteins,
  b) measuring the emission for each of the plurality of fluorescent proteins with each of the optical bandpass filters and scaling the emission from cold to hot, wherein cold represents low emission and hot represents high emission for each optical bandpass filter-fluorescent protein combination,
  c) building a two-dimensional matrix for the scaled emission for each of the plurality of fluorescent proteins with each of the optical bandpass filters,
  d) selecting a first test fluorescent protein and identifying a first test optical bandpass filter for the first test protein that is as hot as possible for the test fluorescent protein in the two dimensional matrix while being cold for at least a second and a third test fluorescent protein to produce a first fluorescent protein-optical bandpass filter combination,
  e) repeating step d) for the second and the third test fluorescent proteins to produce second and third fluorescent protein-optical bandpass filter combinations, and
  f) selecting the first, second and third selected optical bandpass filter-fluorescent protein combinations for simultaneous measurement of three fluorescent proteins.

Using the method described herein, three fluorescent proteins can be selected for simultaneous detection in order to minimize spectral overlap and thus facilitate more accurate measurements. The best bandpass filter for each protein is also selected. In one embodiment, the emission for each of the plurality of fluorescent proteins with each of the optical bandpass filters is expressed as a mid-range value, that is, the middle of the fluorescence measured.

In one embodiment, the selection is performed with six filters 1) Pacific Blue-A, 2) AmCyan-A, 3) FITC-A, 4) PE YG-A, 5) PE-Cy-5.5 YG-A, 6) PE-TxRed YG-A.

A "DNA part" is a finite sequence of nucleotides with a particular function, for example, a coding sequence for a specific protein (CDS), a promoter (P), a sequence that facilitates the expression of a gene such as an inducer or a repressor, a ribosome binding site (RBS) or a terminator. The problem is that many parts have not been characterized well. They haven't always been tested to show what they do, and even when they have, their performance can change with different cell types or under different laboratory conditions.

A "circuit" is a collection of DNA parts, e.g., one or more transcription units, that encodes a protein or protein fragment, such as a reporter protein and/or a protein fragment having a particular function. The DNA parts of the circuit interact to activate or repress expression of each part. When the circuit is transfected into a cell, the expression of the circuit will cause the cell to respond in a certain predictable way. For example, expression of a circuit can cause a cell to take on a particular shape or structure, or can cause the cell to respond in a certain way to its environment, e.g., to grow towards light, or away from light.

A "transcription unit" is a sequence of nucleotides that includes the coding sequence for a reporter protein operably linked to regulatory sequences that allow for expression of the reporter protein when the transcription unit is contained in a cell and the cell is incubated under conditions suitable for expression of the reporter protein. The reporter protein can, for example, be under the control of a constitutive promoter, an inducible promoter, a repressible promoter or a hybrid promoter.

The term "expression control sequence" refers to promoters, enhancer elements, and other nucleic acid sequences that contribute to the regulated expression of a given nucleic acid sequence. As used herein, the term "enhancer element" refers to a cis-acting nucleic acid element, which controls transcription initiation from homologous as well as heterologous promoters independent of distance and orientation. Preferably, an "enhancer element" also controls the tissue and temporal specification of transcription initiation. In particular embodiments, enhancer elements include, but are not limited to, the UAS control element.

A "DNA promoter" is a DNA sequence that facilitates transcription of a gene. The promoter is typically located at the 5' end of the gene (or transcription unit) that the promoter regulates. Promoters contain DNA sequences and response elements that provide an initial binding site for the RNA transcriptional machinery (including RNA polymerase and transcription factors that recruit the RNA polymerase). Transcription factors bind specific activator and repressor sequences that attach to certain promoters and regulate gene expression.

Promoters can be various lengths. As used herein, a promoter is typically 5 nucleotides to 4000 nucleotides in length or longer, e.g., 10 nucleotides to 2000 nucleotides in length or longer, 20 nucleotides to 1000 nucleotides in length or longer, 30 nucleotides to 500 nucleotides in length or longer, 40 nucleotides to 300 nucleotides in length or longer, e.g., 50 nucleotides to 200 nucleotides in length or longer, 60 nucleotides to 100 nucleotides in length or longer, or 70 nucleotides to 90 nucleotides in length or longer. In some embodiments, a promoter is less than 5 nucleotides in length. In some embodiments, a promoter can be 5 nucleotides to 50 nucleotides in length, 10 nucleotides to 60 nucleotides in length, 20 nucleotides to 70 nucleotides in length, 50 nucleotides to 150 nucleotides in length, 60 nucleotides to 200 nucleotides in length or 80 nucleotides to 250 nucleotides in length, 100 nucleotides to 500 nucleotides in length or 300 nucleotides to 1000 nucleotides in length. The test promoters are typically, e.g., 5 nucleotides, 20 nucleotides, 50 nucleotides, 100 nucleotides, 150 nucleotides, 200 nucleotides, 300 nucleotides, 500 nucleotides, 1000 nucleotides, 2000 nucleotides, 3000 nucleotides in length or longer.

As promoters are typically immediately adjacent to the gene in question, positions in the promoter are designated relative to the transcriptional start site, where transcription of RNA begins for a particular gene, such as a gene encoding a reporter protein. Thus, positions upstream of the gene are negative numbers counting back from −1, for example −100 is a position 100 base pairs upstream of the gene whose expression is regulated. A promoter is typically located at least 35 nucleotides upstream of the transcription start site of the gene, e.g., the gene encoding a fluorescent protein. The test promoter can begin, e.g., −40, −50, −70, −80 or −100 nucleotides or more upstream from the transcriptional start site.

"Constitutive" promoters are those that drive expression continuously under most environmental conditions and states of development or cell differentiation. An exemplary constitutive promoter that is useful as a control promoter is the Hef1a promoter. For example, the DNA part available as BioBricks reference BBa_K511801 includes the Hef1a promoter fused to the mKATE fluorescent protein gene.

An inducible promoter is one that is activated or repressed in response to either the presence of a particular compound, i.e., the inducer, or to a defined external condition, e.g., elevated temperature. An inducible promoter can be activated or repressed by a small molecule such as an antibiotic or by a protein product. An exemplary inducible promoter can be activated by tTA/rtTA transactivator variants in the presence of tetracycline analogues and can be repressed by variants of the LacI transcriptional repressor, such as the TRE-Tight-LacOid promoter (BioBricks reference BBA_k511004).

As used herein, a "hybrid promoter" can contain multiple elements, e.g., multiple synthetic elements, or elements from different promoter regions. A hybrid promoter can contain one or more enhancer elements and one or more activation sequences, and/or elements that are differentially regulated. The invention is further illustrated by the following non-limiting examples.

EXAMPLE 1

Characterization of the Lac-Repressor-HEF1a-LacO1Oid Response Element Pair

Figure 5:
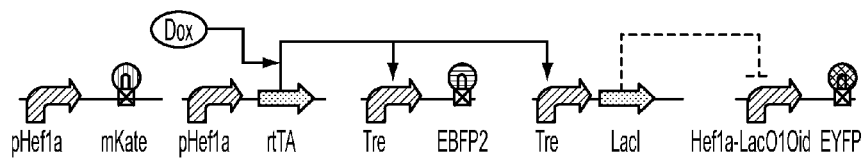
FIG. 5 shows an exemplary multiplex test circuit.

The multiplex circuit to be characterized is shown in FIG. 5.

The constitutive reporter protein transcription unit comprises a constitutive genetic element (pHef1a) and a coding sequence for a constitutive reporter protein (mKate). The mKate constitutive reporter has a red fluorescence emission.

Both the regulatory protein transcription unit and the input reporter protein transcription unit are under the control of the small molecule effector doxycycline (dox). In this example, the activity of the small molecule effector (dox) is mediated through an effector transcription unit. The effector transcription unit comprises a constitutive effector genetic element (pHef1a) and a coding sequence for an effector-regulated protein (rtTA), wherein the constitutive effector genetic element (pHef1a) controls expression of the effector-controlled protein (rtTA).

The regulatory protein transcription unit comprises a genetic element responsive to a small molecule effector (Tre) and a coding sequence for the regulatory protein (LacI), wherein the genetic element responsive to the genetic element responsive to the effector-regulated protein (Tre) controls expression of the regulatory protein (LacI). In the present case, the genetic element responsive to the effector-regulated protein (Tre) is responsive to the effector-controlled protein (rtTA).

The input transcription unit comprises a genetic element responsive to a small molecule effector (Tre) and a coding sequence for the input reporter protein (EBFP2), wherein the genetic element responsive to the effector-regulated protein (Tre) controls expression of the input reporter protein (EBPF2). The genetic element responsive to the effector-regulated protein (Tre) is responsive to the effector-controlled protein (rtTA). The input reporter protein EBFP2 has a blue fluorescence emission.

Because both the expression of the regulatory protein and the input reporter protein are controlled by the genetic element responsive to a small molecule effector (Tre), it is believed that the molar amounts of the regulatory protein and the input reporter protein will be approximately the same.

The output transcription unit comprising a genetic element responsive to the regulatory protein (Hef1a-LacO1Oid) and a coding sequence for the output reporter protein (EYFP), wherein the genetic element responsive to the regulatory protein (Hef1a-LacO1Oid) controls expression of the output reporter protein (EYFP). The output reporter protein EYFP has a yellow fluorescence emission.

In this example, the constitutive transcription unit, input transcription unit, output transcription unit, regulator transcription unit and the effector transcription unit are all on separate plasmids which are transfected into cells simultaneously. The plasmids contain bacterial growth and selection machinery. The constitutive transcriptional unit contains a constitutive promoter (i.e. Human Elongation Factor 1 alpha (Hef1a), CAG (CMV variant), CMV, UBC . . . ). The input transcriptional unit consists of an inducible activatable promoter (i.e. Tet responsive element (TRE), Rheo switch system . . . ). The regulation unit either comprises a "hybrid promoter" that is both activatable and repressible (i.e., activates by Gal4VP16 and is repressed by TALI) or a Constitutive promoter that has the addition of DNA binding sites for the repressors to bind and cause repression (i.e. Hef1a-LacO0Oid).

The cells are grown under conditions suitable to allow transcription/translation of the transcription units. In addition, different populations of cells are exposed to different concentrations of small molecule effector, doxycycline. Standard cell culture practices were used. The HEK 293 FT cell line and derivative cell lines were cultured in DMEM medium (CellGro) supplemented with 10% FBS (PAA Laboratories), 2 mM L-Glutamine (CellGro), 100× Strep/pen (CellGro), 100× Non-Essential amino acids (NEAA) (HyClone), and 10,000× Fungin (Invivogen). Selection was done with 2 ug/ml of puromycin (Invivogen) for 2-4 days or until control cells that did not contain puromycin resistance were dead. Trypsin 0.05% was used to passage the cells.

The cells are then subjected to FACS analysis and the amounts of input, output and constitutive protein fluorescence is measured for each cell. In preparation of cells for FACS analysis the media is suctioned off and appropriate amount of trypsin is added to the cells and then incubated for up to 5 min. The cells are then re-suspended using media supplemented with serum to inactivate the trypsin. The cells are then spun down at a speed of 100×g for 10 min, the supernatant is removed and the cells are re-suspended in 1×PBS (phosphate buffered saline) in the appropriate volume. These cells are then put through the flow cytometer for measurements.

While the colors for the input, output and constitutive protein fluorescence are selected to have as little overlap as possible, there is some inherent overlap between the different colors. Color compensation is a process by which the fluorescence spillover originating from one fluorophore other than the one being detected is subtracted from the one being detected, usually as a subtraction. In order to reduce the signal overlap, color compensation is employed on the measured levels of the input reporter protein (EBPF2), the output reporter protein (EYFP) and the constitutive reporter protein (mKate) to reduce signal overlap and produce a compensated level of input reporter protein (EBPF2), a compensated level of output reporter protein (EYFP), and a compensated level of constitutive reporter protein (mKate).

Color compensation can be a linear color compensation in which a fixed percentage of signal is subtracted or a non-linear compensation. The term non-linear compensation includes a piecewise linear fit, in which the expression of a color is measured on two FACS laser/filter combinations, one of which is the primary channel and one of which is the channel to be compensated. It may be useful to use an input effector like a small molecule inducer in order to get sufficient range of expression of the fluorescent protein. The data is segmented into bins on the primary channel value, then mean and standard deviation of points within that bin are measured on the channel to be compensated. This information forms the non-linear model. In order to perform compensation, we take a set of measurements and solve for a set of primary channel expression values that would superpose to produce the measured set of raw measurements (e.g. by iteration until convergence).

Color compensation also includes autofluorescence compensation, that is, compensating for the autofluorescence of the cells themselves.

Figure 6:
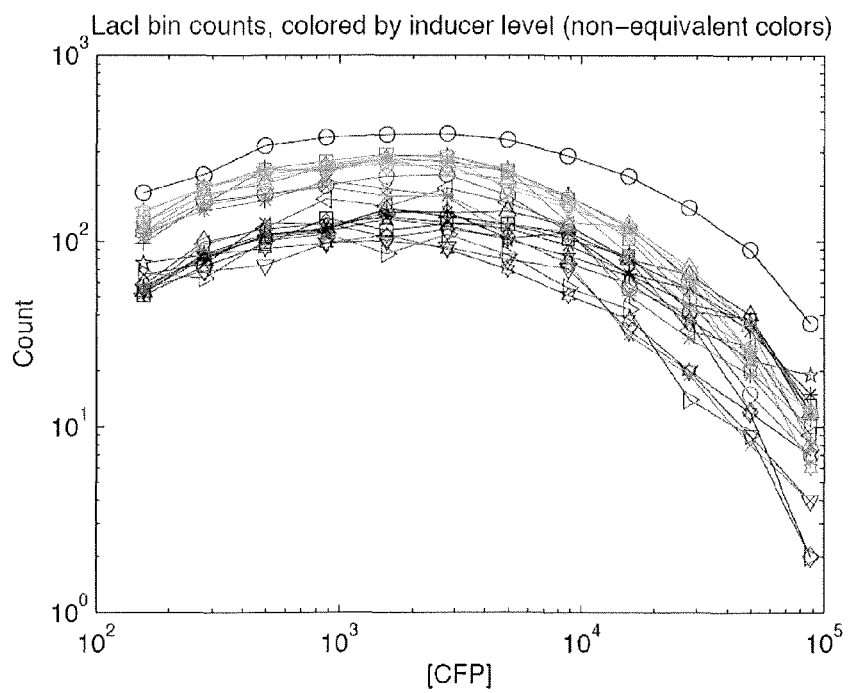
FIG. 6 shows the bin counts from 2-dimensional binning for the circuit of FIG. 5.

Once color compensation on the three signals is completed, two dimensional segmentation, that is, binning is performed. For each concentration of small molecule effector employed (dox), cells are binned into equally spaced bins according to their compensated level of constitutive reporter protein (mKate) to produce a plurality of equally spaced bins. Binning of the cells reduces the noise associated with measuring levels in individual cells. For each bin, a bin average level of constitutive reporter protein (mKate) is computed or the bin-center value might be used to represent the bin. For this example, the bin center was used as the representative of the bin. FIG. 6 shows the results of 2-dimensional binning for the current example.

Optionally, the fluorescent color translation is performed on the compensated level of input reporter protein (EBPF2), compensated level of output reporter protein (EYFP), and average level of constitutive reporter protein (mKate). Because the input, output and constitutive reporters have different colors, they do not have the same "units." Thus, color translation allows conversion of the three different colors into the same units so that the measured values for the three colors can be directly compared. In order to effect the color translation, an experiment was run with three constitutively produced colors. These colors were induced with the same promoter which allowed linear mapping between the colors, e.g., how many units of EBFP2/Pacific Blue-A equals one unit of mKate/PE-TxRed YG-A.

After binning and optional fluorescent color translation, normalization is performed for the cells in each bin. The compensated level of output reporter protein (EYFP) and/or the compensated level of input reporter protein (EBPF2) is normalized by the average level of constitutive reporter protein (mKate) to produce a normalized level of input reporter protein (EBPF2) and/or a normalized level of output reporter protein (EYFP).

Once the input and output fluorescence are normalized, transfer curves are produced for either the small molecule effector (dox) or for the regulatory protein (LacI)

Figure 7:
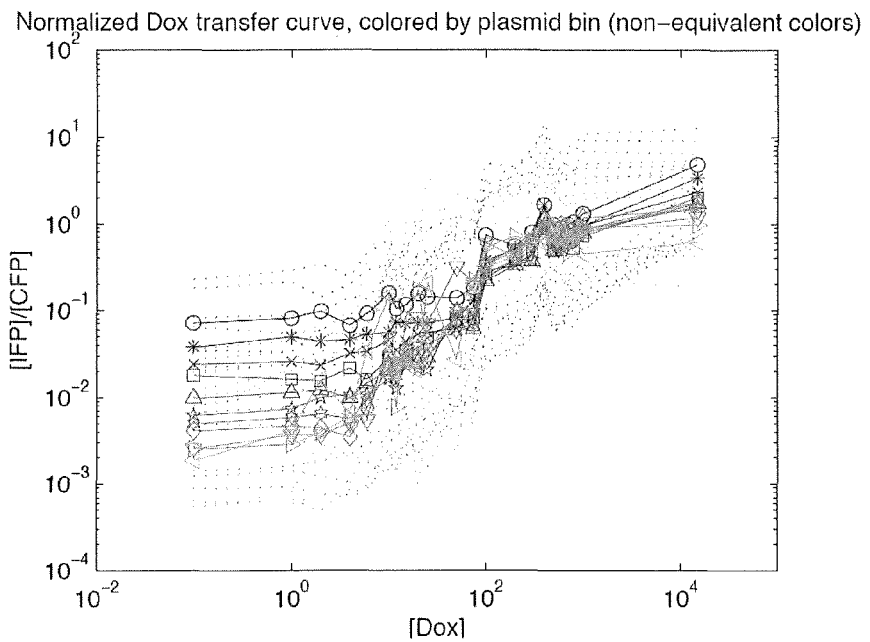
FIG. 7 shows a normalized small molecule effector transfer curve of the normalized level of input reporter protein versus the amount of small molecule effector.

A normalized small molecule effector transfer curve of the normalized level of input reporter protein versus the amount of small molecule effector is shown in FIG. 7. Each point represents a separate bin of cells.

This transfer curve shows that for the dox levels less than or equal to 3 nM the level of IFP stays low regardless of the plasmid count and for dox levels more than 200 nM the level of IFP saturates at a high value. Note that the level of IFP and the amount of LacI being produced are positively correlated. The curve validates the activation of Tre in the presence of rtTA and high levels of Dox.

Figure 8:
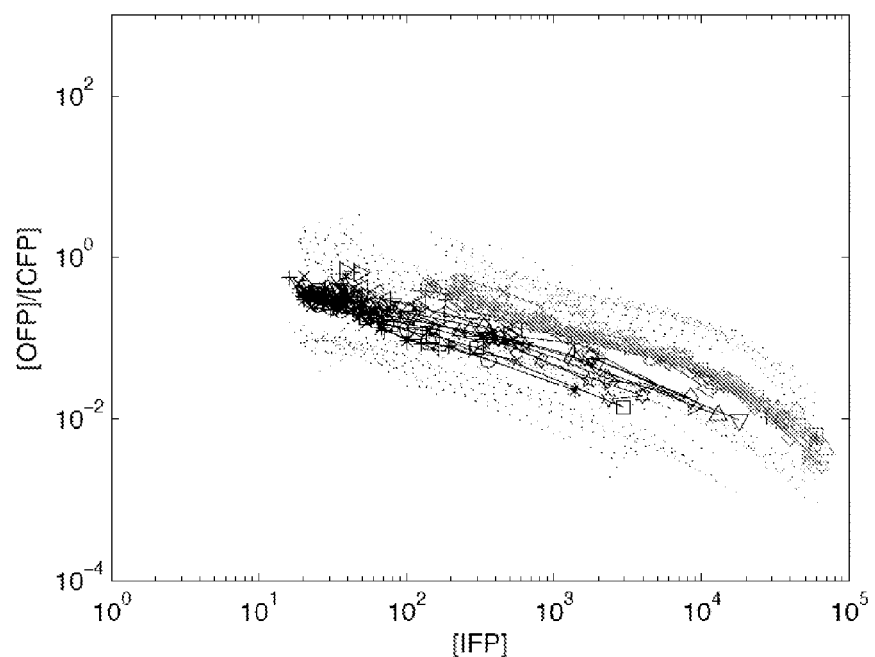
FIG. 8 shows a normalized regulatory protein transfer curve of the normalized level of output reporter protein versus the compensated level of input reporter protein.

A normalized regulatory protein transfer curve of the normalized level of output reporter protein versus the compensated level of input reporter protein is shown in FIG. 8. Each line represents a different amount of small molecule effector (dox)

This transfer curve shows that the output of the Hef1a-Laco1Oid can be repressed by LacI 100-fold.

EXAMPLE 2

Characterization of the Tal1-Repressor-UAS-T1 Response Element Pair

The multiplex circuit to be characterized is shown in FIG. 9.

The constitutive reporter protein transcription unit comprises a constitutive genetic element (pHef1a) and a coding sequence for a constitutive reporter protein (EBFP2). The EBFP2 constitutive reporter has a blue fluorescence emission.

he regulatory protein transcription unit and the input reporter protein transcription unit, which are co-expressed in this example, are under the control of the small molecule effector doxycycline (dox), which binds to the constitutively expressed protein rtTA to regulate transcription from the Tre genetic element.

In this example, the effector transcription unit comprises a constitutive effector genetic element (CAG) and a coding sequence for an effector-regulated protein (rtTA), wherein the constitutive effector genetic element (CAG) controls expression of the effector-controlled protein (rtTA). In this example, the effector transcription unit further comprises coding sequence for the VP16-GAL4 activator which binds UAS-T1 in the output transcription unit. In the absence of dox, Tal1 is not expressed and the constitutively expressed VP16-GAL4 activator binds to UAS-T1, leading to expression of the mKate output reporter. The effector transcription unit contains a coding sequence for a 2A self-cleaving peptide allowing for expression of rtTA and VP16-GAL4 from the same construct.

The test regulatory protein transcription unit and the input transcription unit are co-expressed from a genetic element responsive to a small molecule effector (Tre). When dox is added to the system, it binds to rtTA and the activated rtTA binds to the Tre element, thus activating transcription of the test regulatory protein (Tal1) and the input reporter protein (EYFP). The combination test regulatory protein transcription unit and the input transcription unit contains a coding sequence for a 2A self-cleaving peptide allowing for expression of Tal1 and EYFP from the same construct. The input reporter protein EYFP has a yellow fluorescence emission.

The output transcription unit comprises a genetic element responsive to the regulatory protein (UAS-T1) and a coding sequence for the output reporter protein (mKate), wherein the genetic element responsive to the regulatory protein (Tal1) controls expression of the output reporter protein (mKate). In the absence of dox, VP16-Gal4 binds to the UAS-T1 and activates production of mKATE. However, in the presence of dox, Tal1 is produced which represses UAS-T1 and this represses production of the mKate output reporter. The output reporter protein mKate has a red fluorescence emission. In the presence of the small molecule effector (dox), the activator protein VP16-Gal4 is expressed, which activates the UAS-T1 upstream activation sequence. In the presence of Tal1, the test regulatory protein, the production of the output reporter protein is repressed.

The data analysis was performed substantially as in example 1.

Figure 10:
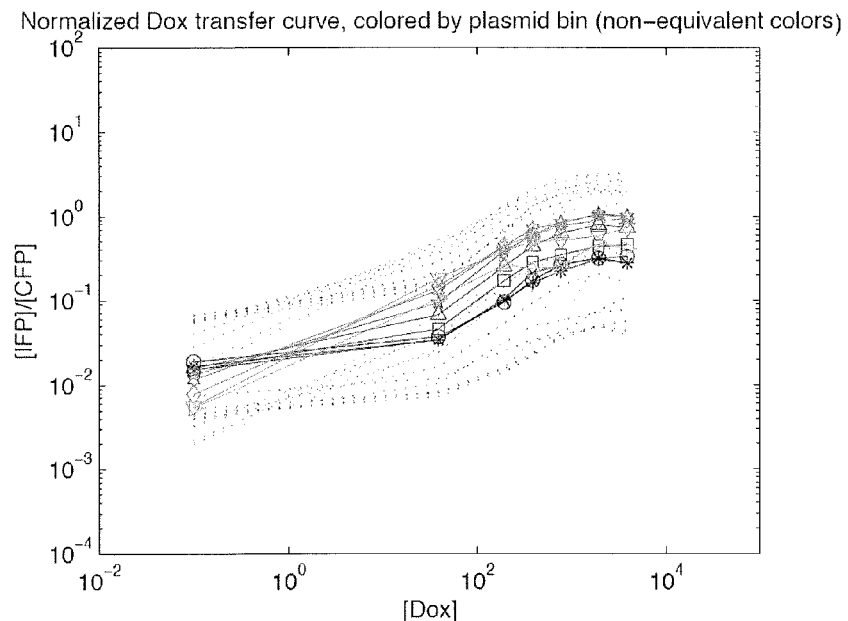
FIG. 10 shows a normalized small molecule effector transfer curve of the normalized level of input reporter protein versus the amount of small molecule effector.

A normalized small molecule effector transfer curve of the normalized level of input reporter protein versus the amount of small molecule effector is shown in FIG. 10. Each line represents a separate bin of cells.

This transfer curve shows that for the dox levels less than or equal to 3 nM the level of IFP stays low regardless of the plasmid count and for dox levels more than 200 nM the level of IFP saturates at a high value. Note that the level of IFP and the amount of Tal1 being produced are positively correlated. The curve validates the activation of Tre in the presence of rtTA and high levels of Dox and it is consistent with the curve in FIG. 7.

Figure 11:
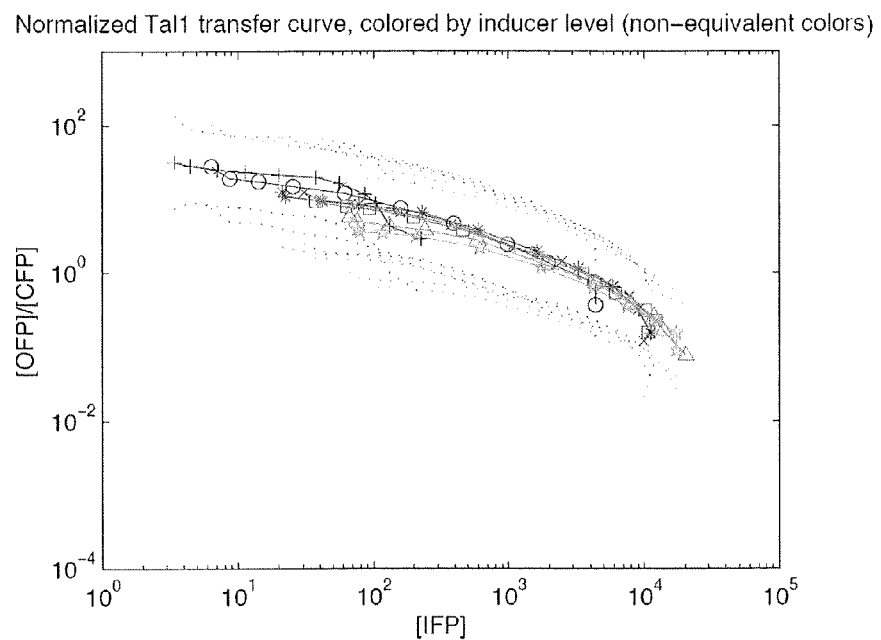
FIG. 11 shows a normalized regulatory protein transfer curve of the normalized level of output reporter protein versus the compensated level of input reporter protein.

A normalized regulatory protein transfer curve of the normalized level of output reporter protein versus the compensated level of input reporter protein is shown in FIG. 11. Each line represents a different amount of small molecule effector (dox)

This transfer curve shows that the output of the UAS-T1 can be repressed by Tal1 100-fold.

EXAMPLE 3

Characterization of an miRNA Regulatory Molecule

Figure 12:
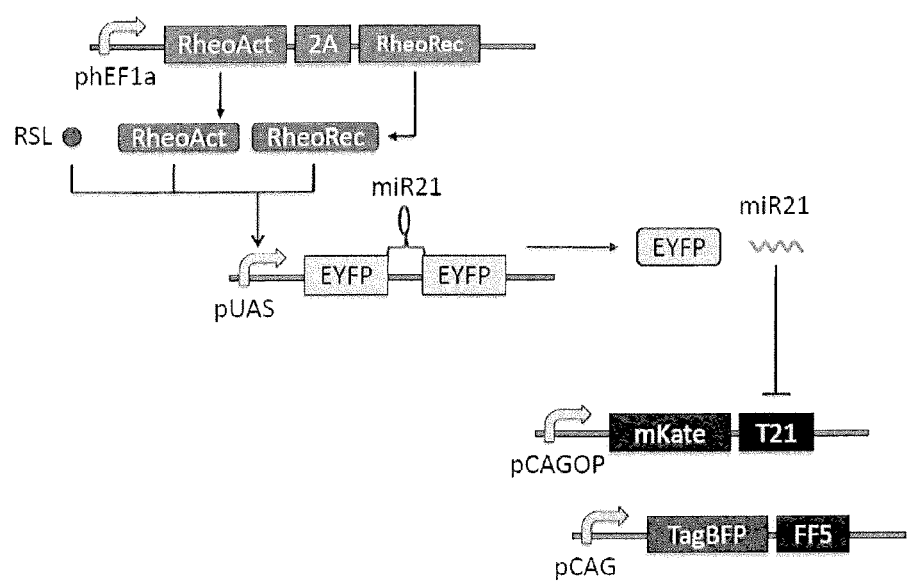
FIG. 12 shows an embodiment of an miRNA circuit, the miR21 low circuit.

FIG. 12 shows an embodiment of an miRNA circuit, the miR21 low sensor.

The effector transcription unit includes the RheoSwitch system in which the Rheoreceptor and Rheoactivator proteins are activated by the presence of RSL1 ligand. In the presence of the RSL1 ligand, the receptor and activator stably dimerize and bind to the response element and turn on transcription. The effector transcription unit contains the RheoAct and RheoRec genes under control of a phEF1a promoter. The 2A self-cleaving sequence allows both proteins to be produced in the same construct. In the presence of the RSL effector, the RheoAct-RheoRec complex binds the pUAS promoter in the input transcription unit to activate transcription.

The test regulatory molecule transcription unit and the input transcription unit are co-expressed from a single pUAS. The input reporter protein is EYFP. The test regulatory molecule is the miR21 miRNA.

The output reporter transcription unit comprises the mKate under control of a pCAGOP promoter. The LacI-controlled promoter CAGop is a LacI repressed promoter (CAG promoter followed by an intron with two LacO sites). Thus, in the absence of LacI, this promoter is activated.

The output reporter transcription unit contains the T21 sequence for post-transcriptional regulation of mKate production by the miR21 test regulatory molecule.

The constitutive transcription unit contains a pCAG constitutive promoter controlling expression of a TagBFP blue fluorescent protein constitutive reporter.

Figure 13:
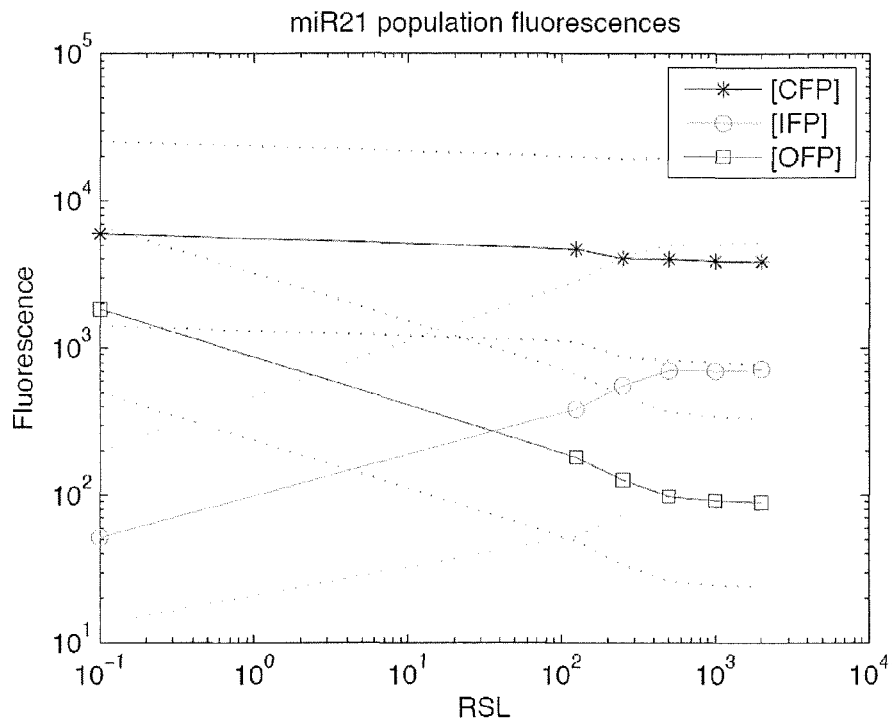
FIG. 13 shows the transfer curves for the miRNA circuit of FIG. 12.
Figure 13:
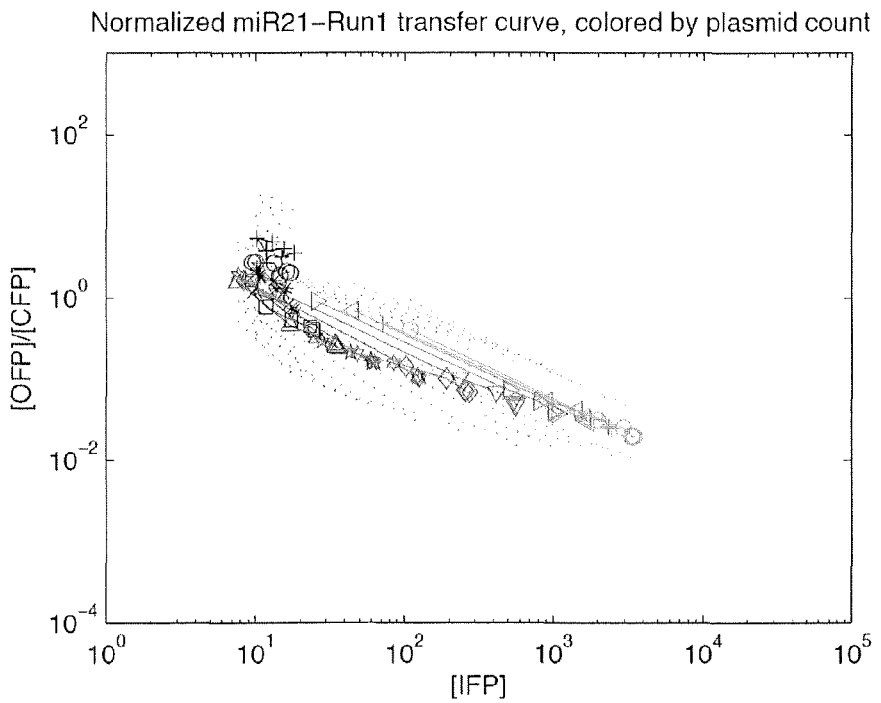

FIG. 13 shows the transfer curves for the miR21 low sensor of FIG. 12. (a) shows the population dynamics which depicts a 12 fold repression whereas in (b) with the methods described here, at least a 50 fold repression is revealed.

FIG. 14 shows the miR21 high miRNA circuit.

The constitutive transcription unit, the effector transcription unit and the test regulatory molecule transcription unit/ input transcription unit are the same as for the miRNA low sensor. The output reporter transcription unit is different. Instead of being directly regulated by the miR21-T21 interaction, the output reporter transcription unit is indirectly regulated via two linking circuits. In this case, a linking circuit is defined as a circuit optionally regulated by a second input effector that links the effect of the test regulatory molecule-test genetic element pair to the output reporter transcription unit. The linking circuit contains the test genetic element while the output reporter transcription unit contains a signal responsive to a linking output from the linking circuit. Linking circuits also allow amplification of the signal from the test regulatory molecule.

In the miR21 high sensor, the output transcription unit includes the mKate output reporter under control of the pCA-GOP promoter and post-transcriptionally regulated by the miRFF4-FF4 pair. Both the LacI protein for regulation of the pCAGOP promoter and the miRFF4 miRNA are on a first linking circuit that is under control of the pTRE promoter, which is activated in the presence of rtTA. The first linking circuit also contains the T21 sequence which is responsive to the presence of the miR21 miRNA. The activation of the pTRE promoter in the first linking circuit is controlled by a second linking circuit which contains a constitutively expressed rtTA gene and a T21 sequence. In the presence of dox, the constitutively expressed rtTA protein is activated and binds to pTRE in the second linking circuit, activating transcription of both LacI and miRFF4. Both LacI and miRFF4 repress production of mKate in the output circuit.

Figure 15:
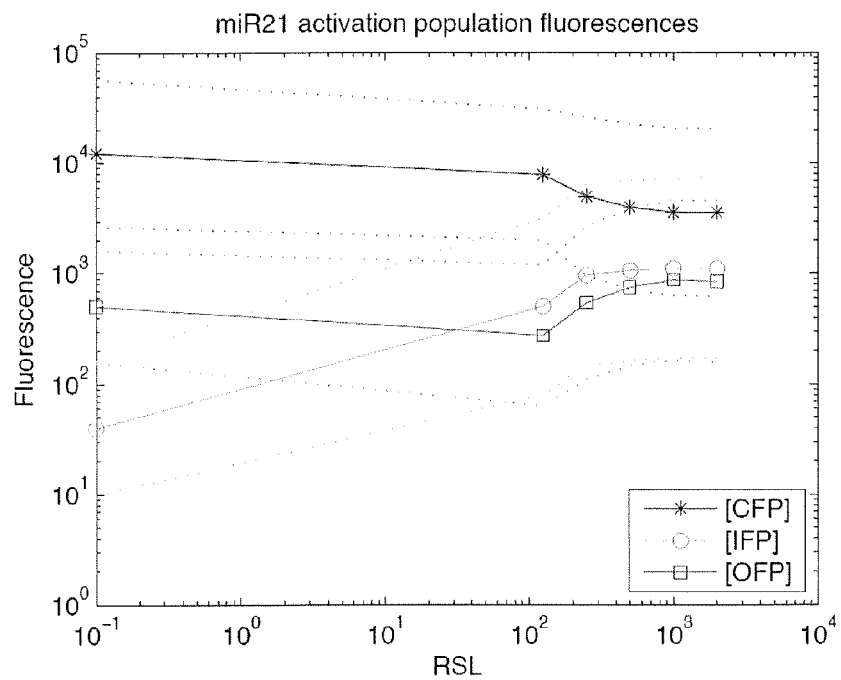
FIG. 15 shows the transfer curves for the miRNA circuit of FIG. 14.
Figure 15:
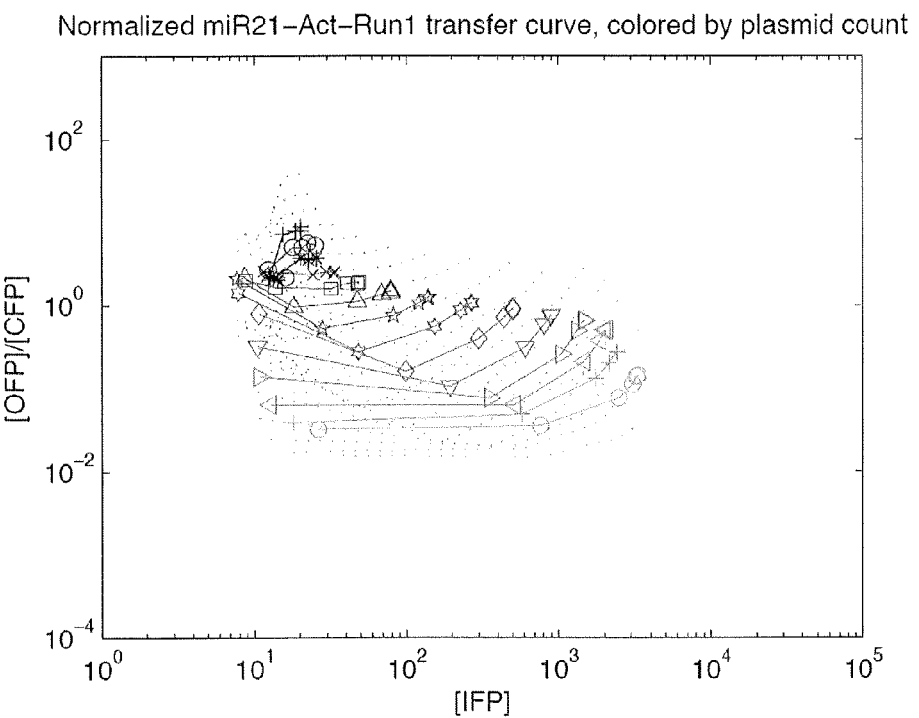

FIG. 15 shows the transfer curves for the miR21 high sensor of FIG. 14. The figure shows the activation relationship strongly correlated with the number of plasmids. The more EYFP (and miR21) exists the more mKate is produced, except for the first data point which might be due mKate expression before sufficient LacI builds up to suppress the mKate production.

EXAMPLE 4

Selection of Three Fluorescent Proteins for Simultaneous Analysis

In order to minimize spectral overlap between the three fluorescent proteins, a novel heat map selection process was developed. The BD LSR II and BD LSR Fortessa FACS machines used for the experiments described herein has six filters, 1) Pacific Blue-A, 2) AmCyan-A, 3) FITC-A, 4) PE YG-A, 5) PE-Cy-5.5 YG-A, 6) PE-TxRed YG-A. Emission was measured for each of the six filters with six different fluorescent protein: Cerulean (cer), EBFP (enhanced blue fluorescent protein), AmCyan1, EYFP (enhanced yellow fluorescent protein), EGFP (enhanced green fluorescent protein) and mKATE. The cer emission can be measured with either the 1) Pacific Blue-A, or 2) AmCyan-A filters. The EBFP emission can also be measured with either the 1) Pacific Blue-A, or 2) AmCyan-A filters. The AmCyan1 emission can be measured with either the 1) Pacific Blue-A, or 2) AmCyan-A filters. The EYFP emission can be measured with the 3) FITC-A filter. The EGFP emission can be measured with the 3) FITC-A filter. The mKATE emission can be measured with the 4) PE YG-A, 5) PE-Cy-5.5 YG-A, or 6) PE-TxRed YG-A filter.

Figure 16:
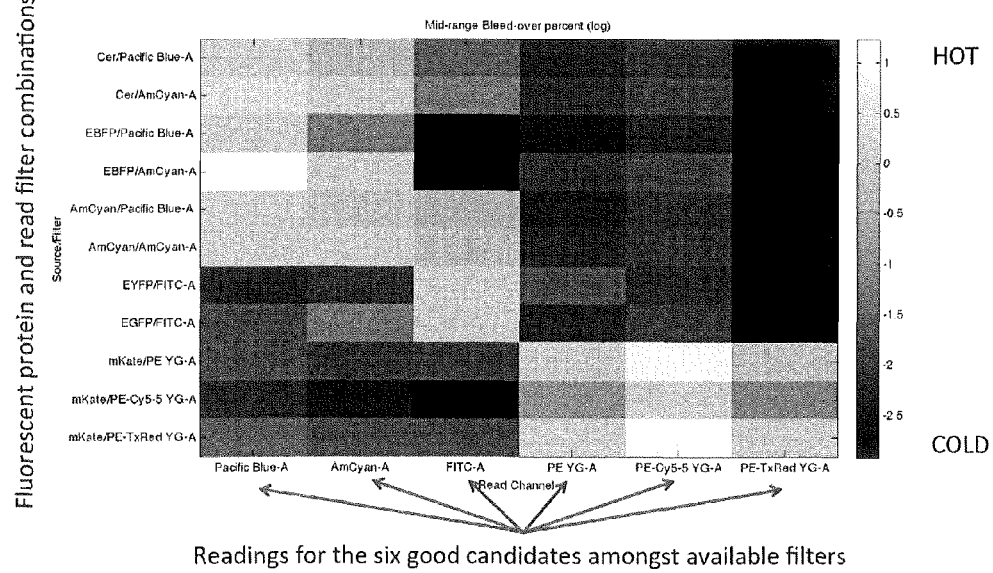
FIG. 16 shows an example of a two-dimensional heat map.

The mid-range bleed-over emission is measured for each of the fluorescent protein/optical bandpass filter combinations and expressed as an index of hotness/coldness. A two-dimensional heat map matrix of the values is then produced. (FIG. 16)

Figure 17:
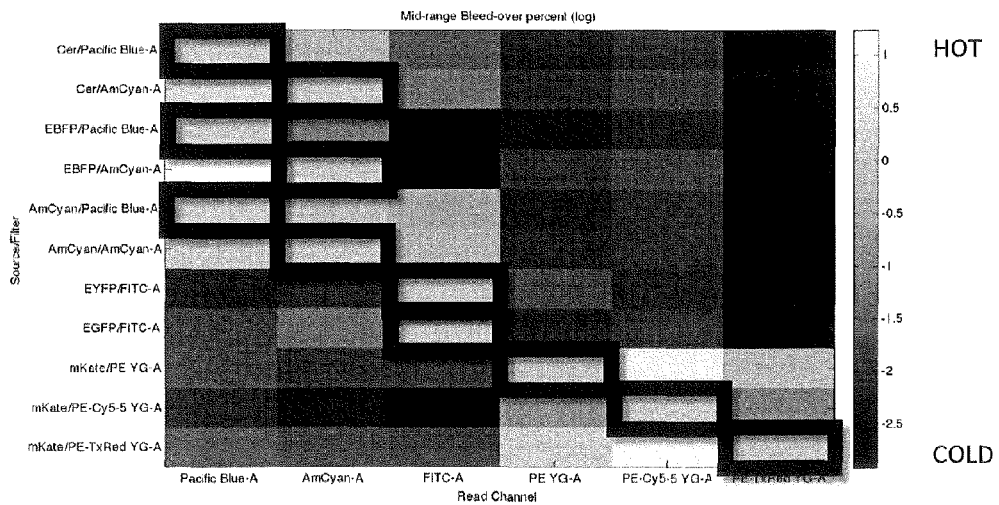
FIGS. 17 and 18 show the setting of one protein emission to zero and scaling the remaining emissions.
Figure 18:
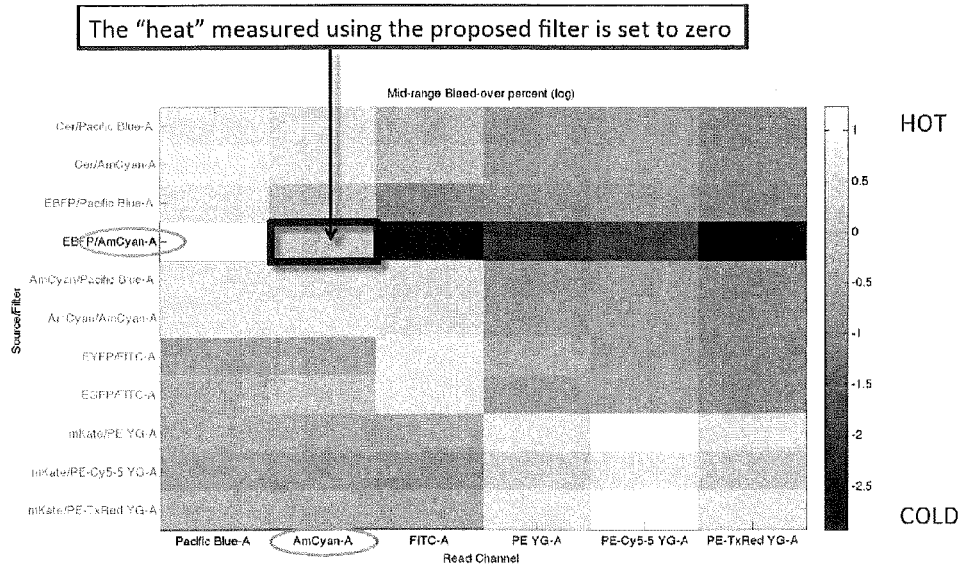
Figure 19:
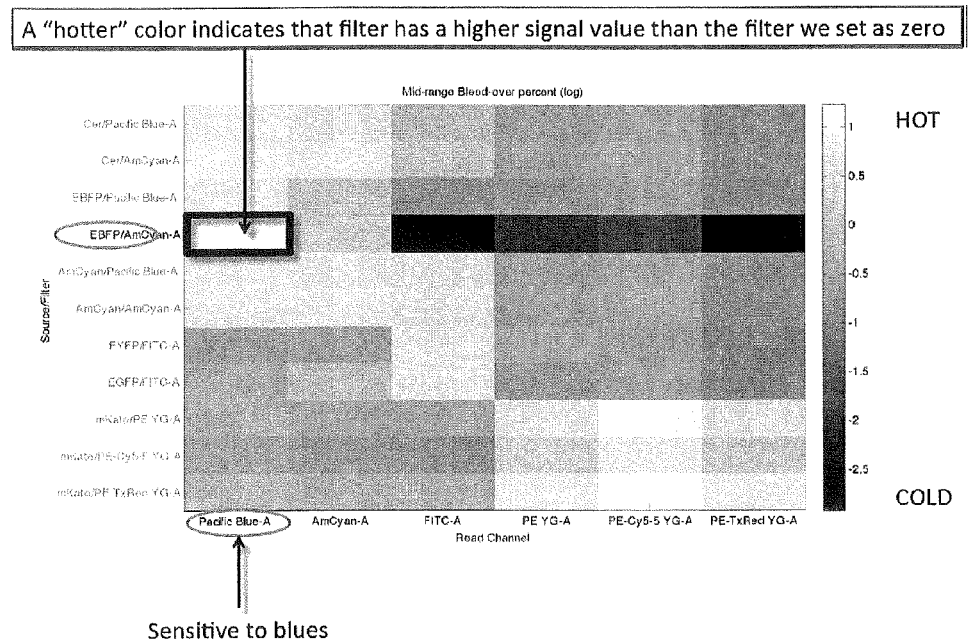
FIG. 19 shows that "hotter" colors signify higher values that the value set to zero.
Figure 20:
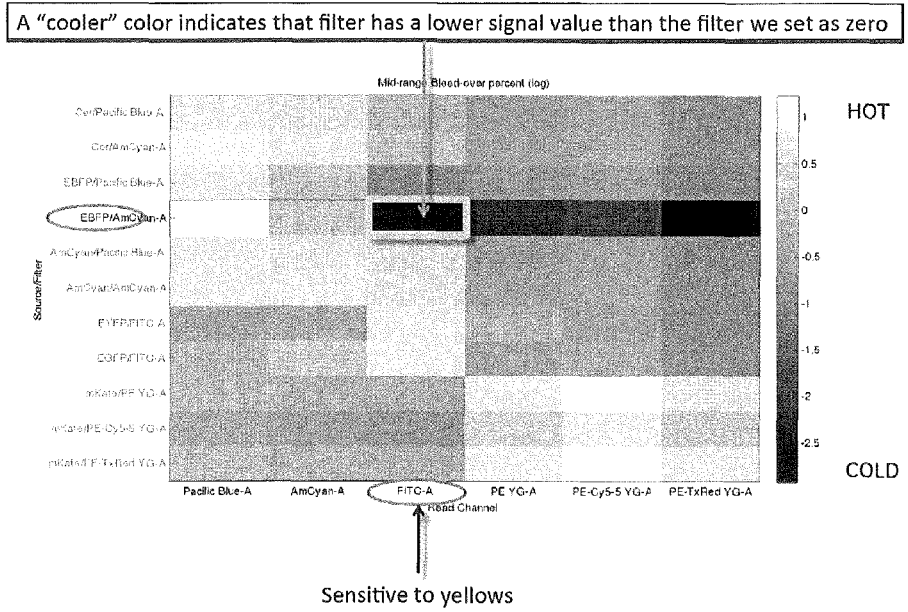
FIG. 20 shows that cooler colors signify lower signal values than the value set to zero.
Figure 21:
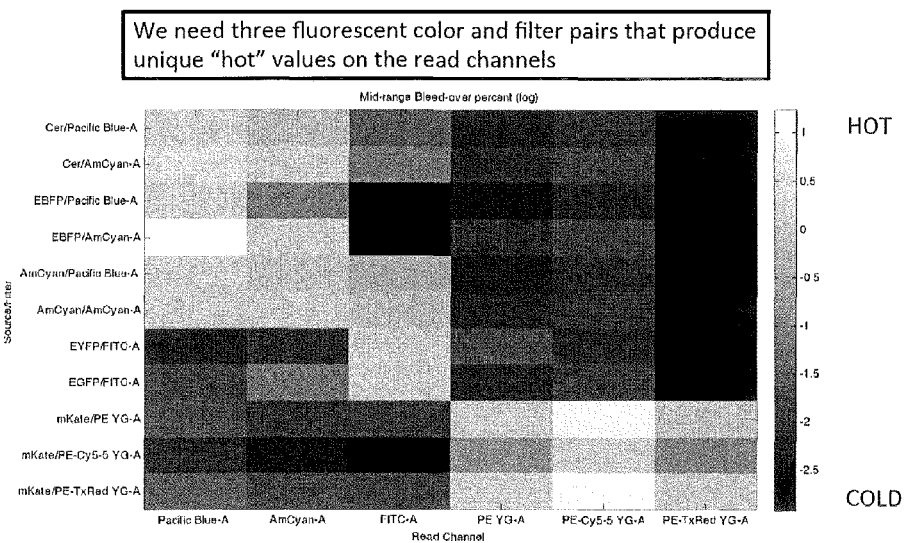
FIG. 21 shows selection of color/filter pairs with unique values.

In one example, the "heat" measured with the AmerCyan-A filter with the EBFP protein is set to zero and the remaining scaled emissions are adjusted accordingly. (FIGS. 17 and 18) A "hotter" color indicates a signal higher than the value that was set to zero (FIG. 19), while a "cooler" color indicates a signal lower than the value set to zero (FIG. 20). By performing this method with different optical bandpass filter-fluorescent protein combinations, three fluorescent color/optical bandpass filter pairs can be selected. (FIG. 21)

Figure 22:
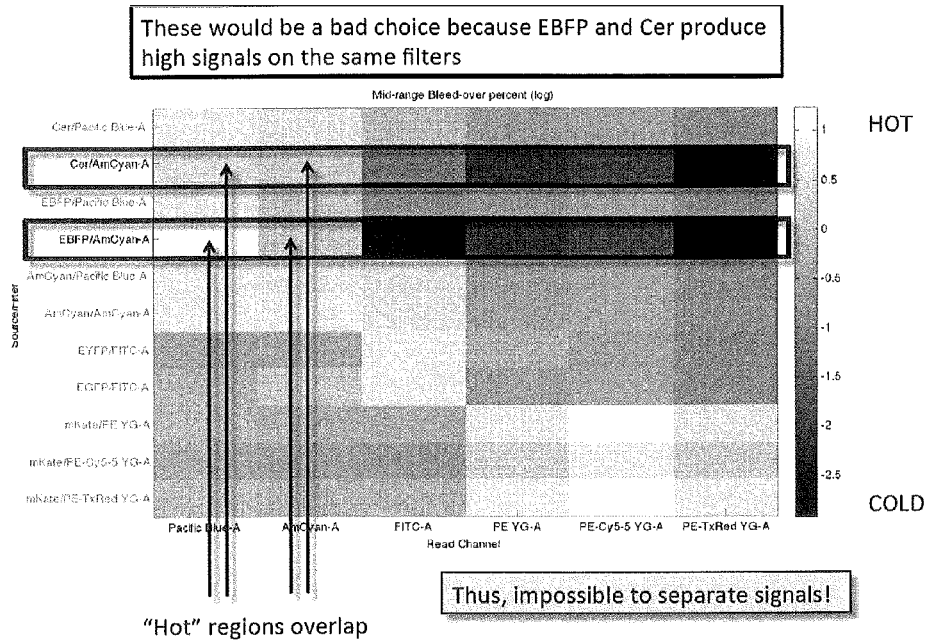
FIG. 22 shows that Cerulian and EBFB should not be used simultaneously with the AmerCyanA filter.

In a specific example, because Cerulian and EBFB both produce hot signals with the AmerCyan-A filter, these two dyes should not be used simultaneously with the AmerCyan-A filter. (FIG. 22)

Figure 23:
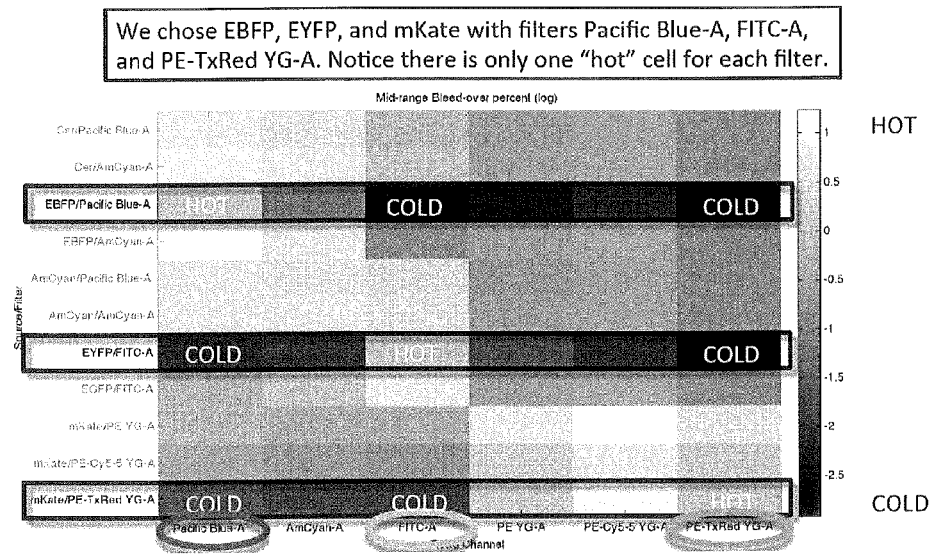
FIG. 23 shows an optimized set of color/filter combinations.

Three fluorescent protein/optical bandpass filter combinations with minimal overlap are EBFP/Pacific Blue-A, EYFP/FITC-A and mKATE/PE-TxRed YG-A. (FIG. 23)

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of evaluating the expression level produced by a test regulatory molecule-test genetic element pair in vitro, comprising providing a sample having a population of cells comprising an effector transcription unit comprising a constitutive effector genetic element and a coding sequence for an effector-regulated protein, wherein the constitutive effector genetic element controls expression of the effector-regulated protein, wherein the effector-regulated protein binds a genetic element responsive to the effector-regulated protein, and wherein the binding activity of the effector-regulated protein to the genetic element responsive to the effector-regulated protein is modulated by an input effector, a test regulatory molecule transcription unit comprising the genetic element responsive to the effector-regulated protein and a coding sequence for the test regulatory molecule, wherein the genetic element responsive to the effector-regulated protein controls expression of the test regulatory molecule, an input transcription unit comprising the genetic element responsive to the effector-regulated protein and a coding sequence for an input reporter protein, wherein the genetic element responsive to the effector-regulated protein controls expression of the input reporter protein, wherein the test regulatory molecule transcription unit and the input transcription unit are on the same genetic molecule element responsive to the effector regulated protein, or are on different expressed separately from separate copies of the genetic molecules element responsive to the effector regulated protein, an output transcription unit comprising the test genetic element responsive to the test regulatory molecule and a coding sequence for an output reporter protein, wherein the test genetic element responsive to the test regulatory molecule controls expression of the output reporter protein, and a constitutive reporter protein transcription unit comprising a constitutive genetic element and a coding sequence for a constitutive reporter protein, wherein the constitutive genetic element controls expression of the constitutive reporter protein, incubating the sample of cells with an amount of the input effector for a time and under conditions sufficient to allow expression of the effector transcription unit, the test regulatory molecule transcription unit, the input reporter protein transcription unit, the output reporter protein transcription unit, and the constitutive reporter protein transcription unit, measuring the levels of the input reporter protein, the output reporter protein and the constitutive reporter protein in individual cells of the sample, two-dimensionally binning the cells to produce a finite number of binned cells, and calculating for each bin a bin average level of constitutive reporter protein, and evaluating the expression level produced by the test regulatory molecule-test genetic element pair from the level of input reporter protein and output reporter protein.

2. The method of claim 1, wherein the test regulatory molecule is a protein or a nucleic acid that regulates transcriptional or post-transcriptional activity.

3. The method of claim 2, wherein the test regulatory molecule is a regulatory protein and the sequence for the test regulatory molecule in the test regulatory molecule transcription unit is a coding sequence for the test regulatory protein.

4. The method of claim 2, wherein the nucleic acid is an miRNA or an siRNA and the sequence for the test regulatory molecule in the test regulatory molecule transcription unit is a DNA sequence encoding the miRNA or siRNA.

5. The method of claim 1, wherein the constitutive effector genetic element, the genetic element responsive to the effector-regulated protein, the test genetic element, or the constitutive genetic element are DNA promoters or upstream activating sequences.

6. The method of claim 3, wherein the constitutive effector genetic element, the genetic element responsive to the effector-regulated protein, the test genetic element, and the constitutive genetic element are DNA promoters.

7. The method of claim 3, wherein the test genetic element is an inducible promoter, a repressible promoter or a hybrid promoter.

8. The method of claim 1, wherein the cell is a mammalian cell.

9. The method of claim 1, wherein the input effector is a physical signal or a small molecule.

10. The method of claim 1, wherein the output reporter transcription unit comprises a plurality of linked transcription units.

11. The method of claim 1, wherein the input reporter protein, the output reporter protein and the constitutive reporter protein are fluorescent proteins.

12. The method of claim 1, wherein the constitutive reporter, the input reporter protein and the output reporter protein are selected from mKATE, enhanced blue fluorescent protein-2 (EBFP2) and enhanced yellow fluorescent protein (EYFP).

13. The method of claim 1, wherein measuring the levels of the input reporter protein, the output reporter protein and the constitutive reporter protein is by flow cytometry.

14. The method of claim 1 further comprising performing signal compensation on the measured levels of the input reporter protein, the output reporter protein and the constitutive reporter protein to reduce signal overlap and produce a compensated level of input reporter protein, a compensated level of output reporter protein, and a compensated level of constitutive reporter protein; or further comprising normalizing, for the cells in each bin, the uncompensated or compensated level of output reporter protein and/or the uncompensated or compensated level of input reporter protein by the bin average level of constitutive reporter protein to produce a normalized level of input reporter protein and/or a normalized level of output reporter protein.

15. The method of claim 14, further comprising translating the uncompensated or compensated level of input reporter protein, the uncompensated or compensated level of output reporter protein, and the uncompensated or compensated level of constitutive reporter protein into standard units to produce an uncompensated translated or compensated translated level of input reporter protein, an uncompensated translated or compensated translated level of output reporter protein, and an uncompensated translated or compensated translated level of constitutive reporter protein.

16. The method of claim 1, wherein the effector transcription unit, test regulatory protein transcription unit, or input transcription unit comprises a coding sequence for an additional protein.

17. The method of claim 16, wherein the additional protein is an additional regulatory protein.

18. The method of claim 1, wherein evaluating the expression level produced by the test regulatory molecule-test genetic element pair is done by producing an input effector transfer curve of the level of input reporter protein versus the amount of input effector, and/or producing a regulatory molecule transfer curve of the level of output reporter protein versus the level of input reporter protein and evaluating the expression level produced by the test regulatory molecule-test genetic element pair from the input effector transfer curve and/or the regulatory molecule transfer curve.

19. The method of claim 11, wherein the three fluorescent proteins can be measured simultaneously.

20. The method of claim 14, wherein color compensation is linear or non-linear.

* * * * *